United States Patent
Goebl et al.

(10) Patent No.: US 10,023,837 B2
(45) Date of Patent: *Jul. 17, 2018

(54) MATERIALS AND METHODS FOR IDENTIFYING AND USING YEAST STRAINS THAT METABOLIZE PENTOSE SUGARS IN THE PRESENCE OF D-GLUCOSE

(71) Applicant: Indiana University Research and Technology Corporation, Indianapolis, IN (US)

(72) Inventors: Mark Goebl, Indianapolis, IN (US); Cary Woods, Indianapolis, IN (US); Ross Cocklin, Indianapolis, IN (US); Josh Heyen, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/260,484

(22) Filed: Sep. 9, 2016

(65) Prior Publication Data

US 2017/0044485 A1    Feb. 16, 2017

Related U.S. Application Data

(63) Continuation of application No. 13/202,452, filed as application No. PCT/US2010/025448 on Feb. 25, 2010, now Pat. No. 9,469,837.

(60) Provisional application No. 61/155,255, filed on Feb. 25, 2009.

(51) Int. Cl.
| | |
|---|---|
| C12N 1/20 | (2006.01) |
| C12N 15/00 | (2006.01) |
| C12P 1/02 | (2006.01) |
| C12P 7/00 | (2006.01) |
| C12Q 1/68 | (2018.01) |
| C07H 21/04 | (2006.01) |
| C12N 1/18 | (2006.01) |
| C12N 15/01 | (2006.01) |
| C12P 7/06 | (2006.01) |

(52) U.S. Cl.
CPC .............. *C12N 1/18* (2013.01); *C12N 15/01* (2013.01); *C12P 7/00* (2013.01); *C12P 7/06* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 5,618,708 A | 4/1997 | Shira et al. | |
| 6,071,729 A | 6/2000 | Jeffries et al. | |
| 2004/0023349 A1* | 2/2004 | Bisgaard-Frantzen | ... C12P 7/10 435/161 |
| 2007/0141675 A1 | 6/2007 | Suga et al. | |
| 2008/0261287 A1 | 10/2008 | Winkler et al. | |

FOREIGN PATENT DOCUMENTS

JP    2009/195220 A    9/2009

OTHER PUBLICATIONS

Fermentis Ethanol Red®. Retrieved from http://www.fermentis.com/wp-content/uploads/2012/06/EthanolRED_EN.pdf on Apr. 13, 2017.*
International Search Report dated Jul. 8, 2010 in connection with PCT/US2010/025448.
Rose, et al. "Glucose repression in *Saccharomyces cerevisiae* is directly associated with hexokinase phosphorylation by hexokinases PI and PII," Eur. J. Biochem. 199:511-518, 1991.
Raghevendran et al. "Phenotypic characterization of glucose repression mutants of *Saccharomyces cerevisiae* using experiments with C13-labelled glucose," Yeast, Jul. 15, 2004;21 (9):769-779.
Bailey, et al., *Saccharomyces cerevisiae* Mutants Resistant to Catabolite Repression: Use in Cheese Whey Hydrolysate Fermentation, Applied and Environmental Microbiology, 1982, 44(3):631-639.
Bailey, et al., Isolation and Characterization of a Pleiotropic Glucose Repression Resistant Mutant of *Saccharomyces cerevisiae*, Mol. Gen. Genet., 1984, 193:507-512.
Gancedo, Yeast Carbon Catabolite Repression, Microbiology and Molecular Biology Reviews, 1998, 62(2):334-361.
Ho, et al., Genetically Engineered *Saccharomyces* Yeast Capable of Effective Cofermentation of Glucose and Xylose, Applied and Environmental Microbiology, 1998, 64(5):1852-1859.
Jin, et al., *Saccharomyces cerevisiae* Engineered for Xylose Metabolism Exhibits a Respiratory Response, Applied and Environmental Microbiology, 2004, 70(11):6816-6825.
Kaniak, et al., Regulatory Network Connecting Two Glucose Signal Transduction Pathways in *Saccharomyces cerevisiae*, Eukaryotic Cell, 2004, 3(1):221-231.
Kotter, et al., Xylose Fermentation by *Saccharomyces cerevisiae*, Appl. Microbiol. Biotechnol., 1993, 38:776-783.
Sedlak, et al., Characterization of the Effectiveness of Hexose Transporters for Transporting Xylose During Glucose and Xylose Co-fermentation by a Recombinant *Saccharomyces* Yeast, Yeast, 2004, 21:671-684.
Toivari, et al., Endogenous Xylose Pathway in *Saccharomyces cerevisiae*, Applied and Environmental Microbiology, 2004, 70(6):3681-3686.

(Continued)

Primary Examiner — Yong D Pak
(74) Attorney, Agent, or Firm — Quarles & Brady LLP

(57) ABSTRACT

Disclosed herein are materials and methods for creating and/or isolating variants of yeasts especially variants of *Saccharomyces cerevisiae* that can grow on sugars other than D-glucose in the presence of amounts of 2-deoxy-glucose and or D-glucose that inhibit most strains of yeast from growing on sugars other than D-glucose. Selection media that can be used to isolate such variants include pentose sugars such as D-xylose, L-glutamine and 2-deoxy-glucose. Mutations in the Grr1 and Red genes in some strains also produce variants that can grow on sugars including the pentose D-xylose in the presence of 2-deoxy-glucose.

12 Claims, 11 Drawing Sheets

(56) References Cited

OTHER PUBLICATIONS

Van Dijken, et al., An Interlaboratory Comparison of Physiological and Genetic Properties of Four *Saccharomyces cerevisiae* Strains, Enzyme and Microbial Technology, 2000, 26:706-714.
Westergaard, et al., A Systems Biology Approach to Study Glucose Repression in the Yeast *Saccharomyces cerevisiae*, Biotechnology and Bioengineering, 2007, 96(1):134-145.
Westergaard, et al., Elucidation of the Role of Grr1p in Glucose Sensing by *Saccharomyces cerevisiae* Through Genome-wide Transcription Analysis, FEMS Yeast Research, 2004, 5(3):193-204.
Examination Report in connection with CA 2753538, dated Feb. 14, 2017.
Examination Report in connection with CA 2753538, dated Jan. 26, 2016.
Examination Report in connection with EP 10746850.6, dated Oct. 8, 2015.
Roca et al. "Engineering of carbon catabolite repression in recombinant xylose fermenting *Saccharomyces cerevisiae*," Applied Microbiology and Biotechnology, vol. 63, No. 5, May 2004, pp. 578-583.
Examination Report in connection with EP 10746850.6, dated Nov. 22, 2016.
Sturley, et al., Genetic Manipulation of Commercial Yeast Strains, Biotechnology and Genetic Engineering Reviews, 1986, pp. 1-28, vol. 4:1, Newcastle upon Tyne, UK.
Galitski, et al., Ploidy Regulation of Gene Expression, Science, Jul. 9, 1999, pp. 251-254, vol. 285(5425).

\* cited by examiner

Conversion of Plant Biomass to Ethanol

Corn Seed
Starch ⟶ α-D-glucose ⟶ Ethanol

Switchgrass
Cellulose 30-40% ⟶ ß-D-glucose ⟶ Ethanol
Xylan 20-30% ⟶ D-xylose ⟶ Ethanol Yeast fermentation D-glucose ⟶ Ethanol

⤏

D-xylose         Ethanol

Fermentation – Classically carried out by domesticated fungi
*Saccharomyces cerevisiae* – Sugar fungus Ferments many hexose (6 carbon) sugars
    D-glucose (cellulose, starch, glycogen)
    D-mannose (mannan)
    D-fructose
    D-galactose Mutant colonies arising from CEN.PK grown on YP plus 2% D-xylose and 0.1% 2-deoxy-glucose are defective in catabolite repression.

1- CDXR1
2- CEN.PK(113-7D)
3- CDXR3
4- CDXR2

Complementation analysis of 2-deoxy-glucose resistant derivatives of CEN.PK.

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Grr1TfF

<400> SEQUENCE: 1
gaagcccaaa aattaaggca ttgca                                         25

<210> SEQ ID NO 2
<211> LENGTH: 27
<212> TYPE: DNA
<213> ORGANISM: Artificial Sequence
<220> FEATURE:
<223> OTHER INFORMATION: Grr1TR

<400> SEQUENCE: 2
tttgaaactg tgtatagaat gtttcgc                                       27

<210> SEQ ID NO 3
<211> LENGTH: 25
<212> TYPE: DNA
<213> ORGANISM: Artificial Sequence
<220> FEATURE:
<223> OTHER INFORMATION: pAG25Tr1
```

```
<400> SEQUENCE: 3
attactttct gcgcacttaa cttcg                                         25

<210> SEQ ID NO 4
<211> LENGTH: 25
<212> TYPE: DNA
<213> ORGANISM: Artificial Sequence
<220> FEATURE:
<223> OTHER INFORMATION: Reg testA

<400> SEQUENCE: 4
agaatatacc atataggaga cgcga                                         25

<210> SEQ ID NO 5
<211> LENGTH: 25
<212> TYPE: DNA
<213> ORGANISM: Artificial Sequence
<220> FEATURE:
<223> OTHER INFORMATION: Reg1 testD

<400> SEQUENCE: 5
tacgactatg gaagctcaag aagtt                                         25

<210> SEQ ID NO 6
<211> LENGTH: 25
<212> TYPE: DNA
<213> ORGANISM: Artificial Sequence
<220> FEATURE:
<223> OTHER INFORMATION: pAG2tTr1

<400> SEQUENCE: 6
attactttct gcgcacttaa cttcg                                         25
```

MATERIALS AND METHODS FOR IDENTIFYING AND USING YEAST STRAINS THAT METABOLIZE PENTOSE SUGARS IN THE PRESENCE OF D-GLUCOSE

PRIORITY CLAIM

Cross-Reference to Related Applications

This application is a continuation application of U.S. patent application Ser. No. 13/202,452, filed Oct. 19, 2011, which represents the U.S. national phase application of PCT International Application No. PCT/US2010/025448 filed Feb. 25, 2010, which claims the benefit of U.S. Provisional Application No. 61/151,255 filed on Feb. 25, 2009, each of which is incorporated herein by referenced in its entirety.

FIELD OF THE INVENTION

Various aspects related generally to strains of *Saccharomyces*, and for methods for developing and using that same, that can grow on sugars other than D-glucose in the presence of substantial levels of D-glucose.

BACKGROUND

Various species of *Saccharomyces* are among the most important industrially grown microorganisms. Long used to leaven bread, produce beer and wine, and as source of food flavorings and micronutrients, these organisms now play a central role in the production of fuel, facilitating the conversion of sugar stocks to ethanol. A metabolically complex organism, yeast is able to grow both aerobically and at least for several generations anaerobically as well. When grown commercially, as in the production of yeast used to support the commercial baking industry, yeasts such as *Saccharomyces cerevisiae* may be grown in aerated fermentation tanks. The growth of yeast under these conditions may be controlled to increase the production of yeast biomass. One way in which this may be accomplished is to schedule the addition of sugars, such as D-glucose, and the rate of oxygen transfer to the yeast to encourage it to grow aerobically. Various strains of *Saccharomyces* may also be grown under conditions designed to maximize the production of ethanol. Often times, when the object is to maximize the conversion of sugar to ethanol the level of oxygen in the fermentation vessel may be reduced relative to the levels of oxygen used in the vessel when the object is to maximize yeast biomass production in order to favor anaerobic growth.

Most strains of *Saccharomyces* have a preference for growth on D-glucose although many strains are known to grow on other naturally occurring hexoses and even some disaccharides as well. The ability of different species of *Saccharomyces* to grow on different sugars and in the presence of different levels of oxygen accounts for much of its commercial utility including the central role that yeast currently plays in the conversion of plant bio-mass into ethanol for the fuel industry.

One of the best known pathways for the production of ethanol by yeast is the fermentation of 6-carbon sugars (hexoses) into ethanol, especially D-glucose (FIG. 1). One widely used feed stock for the production of ethanol is the polysaccharide starch. Starch is a simple polymer that includes D-glucose. Currently, in the United States at least starch derived from corn is the preferred feed stock for ethanol production by *Saccharomyces cerevisiae*. Corn is a nutrient-intense crop and currently only the kernels of the corn are a suitable source of starch/D-glucose for ethanol fermentation using yeast. Another source of sugar for the yeast based production of ethanol is sugar cane. Sugar cane is naturally higher in fermentable sugar and may be preferred substrate for the production of ethanol using yeast. However, corn is more widely grown in the United States than is sugar cane. And because of climate it is very likely to remain that way. In any event, the sustainability of corn-based ethanol production has been called into question, and as sugar cane is not a viable option in the United States the bio-fuels industry is looking for other sources of fermentable feed stocks beside corn and sugar cane.

One highly touted feed stock is cellulose, it is considered more sustainable than corn and more readily available than sugar cane. Cellulose processed to produce fermentable sugars may well be the carbon source of choice for the future of ethanol production. Growing yeast in order to increase yeast biomass or to produce ethanol from stocks such as starch or cellulose, requires pre-fermentation processing steps to degrade the bio-polymer cellulose into sugar units, such as D-glucose, maltose, trisaccharides, and tetrasaccharides that can be readily fermented by yeast.

Regardless of its source six-carbon sugars especially D-glucose are the primary energy source for yeast based fermentation. Most species of *Saccharomyces* that have been characterized grow preferentially on D-glucose. Many of these strains, including many laboratory derived strains of *Saccharomyces* may grow on hexose sugars other than D-glucose, as well as disaccharides and trisaccharides. However, *Saccharomyces* preference for growth on D-glucose is so strong that most variants of this yeast including almost all industrially important strains exhibit catabolite repression, that is, the strains will not ferment sugars other than D-glucose so long as there are detectable levels of D-glucose in the feed stock.

The inability of all examined versions of *Saccharomyces* to vigorously grow on and produce ethanol from sugars other than D-glucose in the presence of D-glucose is unfortunate for the production of yeast biomass and/or ethanol from any feedstock that includes mixtures of fermentable sugars which include D-glucose. For example, D-glucose is liberated by the breakdown of cellulosic biomass into its fermentable components and the presence of D-glucose in the mix of fermentable sugars drastically slows the conversion of the other sugars into ethanol (FIG. 1).

Despite the current technological hurdles to producing ethanol from cellulose the 2007 Energy Independence and Security Act (EISA 2007) mandates that the U.S. rapidly develop technologies to produce cellulosic ethanol to displace imported petroleum. Accordingly, there is a need for novel strains of industrial *Saccharomyces* and for methods of creating these industrial strains that readily convert sugars other than just D-glucose into biomass or ethanol even in the presence of significant amounts of D-glucose. Some aspects of the present invention address these needs.

SUMMARY OF THE INVENTION

Some aspects of the invention include methods for isolating a yeast, comprising the steps of; providing a growth medium, wherein the medium includes 2-deoxy-glucose; xylose, and glutamine and xylose is the sole carbon source; inoculating the medium with at least one strain of yeast; and isolating at least one yeast cell from the medium; wherein said yeast cell grows on D-xylose as a sole carbon source in the presence of about 0.1 wt. % 2-deoxy-glucose. In some embodiments the growth medium includes about 0.03 wt. %

2-deoxy-glucose. In some embodiments the strain growing on or in the media exhibits detectable growth on the media only after about 14 days. In still other embodiments the appearance of detectable growth may only occur after about 21 days, after inoculation.

In some embodiments the medium used to select the yeast strains includes about 2.0 wt. % xylose, and about 0.5 wt. % glutamine, although any concentration of these reagent is sufficient to support growth of specific strains that may be added to the growth media. In some embodiments the isolated yeast strain is a haploid, diploid or strain of Saccharomyces cerevisiae that has a ploidy of greater than two.

In some embodiments, the yeast strains isolated from the media metabolize at least one pentose sugar even in the presence of at least 0.1 wt. % 2-deoxy-glucose. In some embodiment the feed stock includes at least about 0.03 wt. % 2-deoxy-glucose. In some embodiments the strains metabolize at least one hexose sugar other than D-glucose in the presence of at least 0.1 wt. % 2-deoxy-glucose. In some embodiments the growth medium includes about 0.03 wt. % 2-deoxy-glucose. In some embodiments the strain is a spontaneous mutant. While in still other embodiments the strain may be created by a specific event, such as the targeted disruption of an open reading frame by treating the yeast in a manner known to cause a mutation. Methods and reagents for accelerating the rate of mutagenesis include, but are not limited to, exposing yeast to ionizing radiation, UV-light, and reagents that effect DNA structure such as intercalating agents, alkylating agents, DNA adducts and the like.

Still other embodiments of the invention include variants of yeast, comprising strains of Saccharomyces cerevisiae that will grow on at least one pentose sugar as a sole carbon source in the presence of at least 0.1 wt. % 2-deoxy-glucose. In some embodiments the growth medium includes about 0.03 wt. % 2-deoxy-glucose. In some embodiments the variants are haploid, diploid or have a ploidy number greater than two. In some embodiments the variant strain of Saccharomyces cerevisiae is selected from the group consisting of: JH015, CDXR2 and Fermentis Ethanol Red reg1Δ and Fermentis Ethanol Red grr1–/– (GX1) and the like.

Still other embodiments are methods of fermenting sugar sources, comprising the steps of: providing at least one strain of Saccharomyces cerevisiae, wherein the at least one strain of Saccharomyces cerevisiae will grow on at least one pentose sugar in the presence of at least 0.1% 2-deoxy-glucose; supplying a feed stock that includes at least one sugar and growing said yeast strain in the feed stock. In some embodiments the feed stock includes an amount of D-glucose sufficient to support the growth of the yeast strain in the absence of any additional sugar source. In still other embodiments the feed stock includes a fermentable pentose sugar. In yet other embodiments the feed stock includes at least about 0.1% 2-deoxy-glucose. In some embodiment the feed stock includes at least about 0.03 wt. % 2-deoxy-glucose. In other embodiments the feed stocks include a fermentable hexose sugar other than D-glucose, while in other embodiments the feed stock further includes D-glucose.

Still other aspects include methods of creating mutant strains of yeast, comprising the steps of: providing a strain of yeast, for example, a haploid, diploid or higher ploidy strain of Saccharomyces cerevisiae that is competent in at least one of the genes selected from the group consisting of Grr1 and Reg1; deleting the activity of both Grr1 and Reg1 to create a mutant strain; and testing the strain to determine if it will grow on a pentose sugar in the presence of 0.035 wt. % 2-deoxy-glucose.

Additional embodiments include methods of selecting for or identifying a yeast strain, comprising the steps of providing a haploid, or higher ploidy strain of Saccacharomyes cerevisiae that include a mutation in at least one open reading frame selected from the group consisting of: YLR063w, YMR167w, YPL176c, YPL123c, YPL121c, YBR242w, YBR422w, YHR012w, YHR103w, YHR154w, YCL048w, YLR133w, YOR138c, YOR177c, YDR269c, YIL064w, YOL101c, YML124C, YMR116C, YDR028c, YDR074c, YDL088c, and YGR271, wherein open reading frame encodes a functional gene and the mutation in the open reading frame disrupts the activity of the gene encoded in the open reading frame; and growing said strain of Saccharomyces cerevisiae in a media including xylose as the sole carbon source and about 0.1 wt. % 2-deoxy-glucose; and isolating strains of Saccharomyces cerevisiae that grow in the media. In some embodiments the growth medium includes about 0.03 wt. % 2-deoxy-glucose.

Still other embodiments include methods of isolating haploid, or higher ploidy strain of Saccacharomyes cerevisiae yeast strains; comprising the steps of: providing a strain of that includes a functional copy of at least one of the genes encoded by the open reading frames consisting of: YLR063w, YMR167w, YPL176c, YPL123c, YPL121c, YBR242w, YBR422w, YHR012w, YHR103w, YHR154w, YCL048w, YLR133w, YOR138c, YOR177c, YDR269c, YIL064w, YOL101c, YML124C, YMR116C, YDR028c, YDR074c, YDL088c, and YGR271w; introducing a mutation into at least one of the open reading selected from the group consisting of: YLR063w, YMR167w, YPL176c, YPL123c, YPL121c, YBR242w, YBR422w, YHR012w, YHR103w, YHR154w, YCL048w, YLR133w, YOR138c, YOR177c, YDR269c, YIL064w, YOL101c, YML124C, YMR116C, YDR028c, YDR074c, YDL088c, and YGR271w to produce a mutant of Saccharomyces cerevisiae; and growing the mutant of Saccharomyces cerevisiae on a selection medium, wherein the selection medium includes xylose as the sole carbon source and 0.1 wt. % 2-deoxy-glucose; and isolating the mutants that grow on the medium. In some embodiments the growth medium includes about 0.03 wt. % 2-deoxy-glucose.

Some embodiments of the invention include methods of selecting yeast strains, for example, industrial or laboratory strains of Saccharomyces that grow on sugars other than D-glucose including, for example, some of the pentose sugars found in cellulosic biomass in the presence of 2-deoxy-glucose and by proxy in the presence of D-glucose. Some other embodiments include using industrial strains of Saccharomyces that grow on sugars other than D-glucose in the presence of 2-deoxy-glucose to produce additional yeast biomass and/or an end product or by-product of fermentation such as ethanol from a sugar other than D-glucose in the presence of substantial amounts of D-glucose.

Superior performance for producing cellulosic ethanol. Cellulosic biomass has multiple sugars, most importantly, D-glucose and D-xylose. However, yeast metabolic physiology is often subject to catabolite repression, the regulated use of D-glucose to the exclusion of many other sugars. Although this had not been demonstrated for D-xylose or D-xylulose, we have now shown that D-xylose and D-xylulose utilization are also subject to catabolite repression. Accordingly, wild type yeast strains preferentially metabolize D-glucose in the presence of these pentose sugars. Furthermore, we now show that industrial strains of Saccharomyces are subject to catabolite repression for both hexoses and pentoses. This is an important technical barrier to cellulosic ethanol using most yeast strains. To overcome this barrier to multiple sugar fermentation, one needs to eliminate catabolite repression towards D-xylose. One embodiment includes eliminating catabolite repression by removing at least one of the following genes, GRR1, REG1, and HXK2. Some embodiments of the invention include selecting of industrial yeast strains, for example, *Saccharomyces* that grow on sugars other than D-glucose, especially pentoses, in the presence of 2-deoxy-glucose. In some embodiments this is a process that includes selecting variants of industrial *Saccharomyces* that grow on sugar sources other than D-glucose in the presence of substantial levels of 2-deoxy-D-glucose. In some embodiments these strains lack, or at least do not express, effective levels forms of at least one of the following genes, GRR1, REG1, and HXK2. In still other embodiments these genes may be mutated such that they do not produce appreciable levels of active protein.

Some other embodiments include using industrial strains of *Saccharomyces* that grow on sugars other than D-glucose in the presence of 2-deoxy-glucose to produce additional yeast biomass and/or an end product or by-product of fermentation such as ethanol from a sugar other than D-glucose in the presence of substantial amounts of D-glucose.

Some embodiments include a method of fermenting feed stocks that include mixed sugars, including D-glucose, that include the steps of using multiple yeast strains with different metabolic requirements to efficiently produce either biomass or a metabolite such as ethanol. In some embodiments fermentation is carried out using at least two different strains of yeast strains, wherein at least one strain preferentially grow on D-glucose and may even exhibit catabolite repression in the presence of detectable levels of D-glucose while at least one other strains is de-repressed and may ferment sugars other than D-glucose into ethanol and or biomass even in the presence of detectable levels of D-glucose. In some embodiments this method may provide a system allowing for the efficient simultaneous fermentation of D-glucose and pentose sugars such as D-xylose.

A catabolite repression resistant strain of *Saccharomyces cerevisiae*, comprising: a variant of *Saccharomyces cerevisiae* strain CEN.PKgrr1Δ or a variant of *Saccharomyces cerevisiae* strain Ethanol Red GX1, wherein a single cell isolate of the variant strain grows on a solid media, the media including: D-xylose and 2-deoxy-D-glucose, wherein the principle carbon source in the media is the sugar D-xylose and the growth of the variant strain produces a robust colony within two days on the media.

Still other embodiments include catabolite repression resistant strains of *Saccharomyces cerevisiae* comprising, for example, variants of *Saccharomyces cerevisiae* strain CEN.PKgrr1Δ or a variant of *Saccharomyces cerevisiae* strain Ethanol Red GX1, wherein a single cell isolate of the variant strain grows on a solid media including maltose and 2-deoxy-D-glucose, wherein the principle carbon source in the media can be a D-glucose containing sugars including, but not limited to, maltose and the growth of the variant strain producing a robust colony within two days on the media. Still other embodiments include catabolite repression resistant strains of *Saccharomyces cerevisiae* wherein the media includes about 2% D-xylose and about 0.1% 2-deoxy-glucose.

Still other embodiments include variants that grow on media that include about 2% maltose or another D-glucose containing sugar and about 0.1% 2-deoxy-glucose.

Still other embodiments include catabolite repression resistant strains of *Saccharomyces cerevisiae* wherein the variant strain is selected from the group consisting of: the haploid laboratory strains CEN.PK derivatives $C^{DXR1}$, CEN.PK (113-7D), $C^{DXR2}$, and $C^{DXR3}$ and derivatives of the diploid industrial yeast strains Ethanol Red, GX1 and RX4. In some embodiments the catabolite repression resistant *Saccharomyces cerevisiae* strains selected for using the methods disclosed, grows on a solid media wherein the media includes D-glucose as the principle carbon source.

Some embodiments include catabolite repression resistant strains of *Saccharomyces cerevisiae* wherein the variant strain grows on a solid media that includes: 2% D-galactose; and about 0.03%-2-deoxy-glucose, wherein the D-galactose is the principle source of carbon in the media.

Still other embodiments include methods of producing strains of *Saccharomyces cerevisiae*, including some industrial strains, that grow on a sugar other than D-glucose, comprising the steps of: providing a first variant strain of *Saccharomyces cerevisiae*, wherein said variant grows on a sugar, especially pentoses, other than D-glucose in the presence of 2-deoxy-D-glucose; and over-expressing at least one gene isolated from a catabolic pathway that metabolizes a sugar other than glucose in the first variant strain to form a second variant strain.

Additional embodiments include methods of producing variant strains of *Saccharomyces cerevisiae* that grows on pentoses in the presence of D-glucose. In some embodiments the first variant strain is selected, for example, from the group consisting of: GX1, RX4, $C^{DXR1}$, CEN.PK (113-7D), $C^{DXR2}$, and $C^{DXR3}$ wherein the strain may be adapted to express at least one gene isolated from a D-xylose catabolic pathway.

Still other embodiments include methods of growing strains of *Saccharomyces cerevisiae* on sugar sources other than D-glucose comprising the steps of: providing a first strain of *Saccharomyces cerevisiae*, wherein said strain grows on a sugar source, especially pentoses, other than D-glucose in the presence of 2-deoxy-D-glucose; over-expressing at least one gene isolated from a metabolic pathway that catabolizes a sugar, especially pentoses, other than glucose in the first strain to form a second strain; and growing said second strain on a media, wherein the principle carbon source in the media is a sugar other than glucose, especially a pentose.

In some embodiments the first strain is a variant of *Saccharomyces cerevisiae* strain CEN.PK, selected from the group consisting of: $C^{DXR1}$, CEN.PK (113-7D), $C^{DXR2}$, and $C^{DXR3}$ and at least one over-expressed gene is from a D-xylose catabolic pathway.

In still other embodiments the first strain is a variant of the industrial *Saccharomyces cerevisiae* strain Ethanol Red, selected from the group consisting of: GX1 and RX4 and at least one over-expressed gene are from a D-xylose catabolic pathway.

Still additional embodiments include methods for identifying open reading frames involved in catabolite repression in *Saccharomyces cerevisiae*; comprising the steps of: growing a first variant of a strain of *Saccharomyces cerevisiae* that is subject to glucose repression in the presence of D-glucose, or D-glucose and D-xylose, or D-xylose; propagating a second variant of a strain of *Saccharomyces cerevisiae* that is insensitive to glucose repression grown on a primary carbon source other than D-glucose in the presence of either D-glucose, D-glucose and D-xylose, or D-xylose; and comparing the proteomes of the first variant and the second variant to identify differences between the proteomes of the first and the second variants.

In some embodiments D-xylose is replaced by another secondary sugar such as maltose or maltotriose, but not limited to maltose or maltotriose.

The method according to claim 10, wherein the differences between the proteomes of the first and the second variant are indicative of differences in at least one of the products of the following open reading frames: YLR063w, YMR167w, YPL176c, YPL123c, YPL121c, YBR242w, YBR422w, YHR012w, YHR103w, YHR154w, YCL048w, YLR133w, YOR138c, YOR177c, YDR269c, YIL064w, YOL101c, YML124C, YMR116C, YDR028c, YDR074c, YDL088c, and YGR271w.

DETAILED DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

As used herein, unless specified otherwise, the term 'about' means plus or minus 20 percent, for example, about 1.0 encompasses the range 0.8 to 1.2.

As used herein, unless specified otherwise, the term 'detectable growth' means growth including and until evidence of growth is apparent by visual inspection with the unaided human eye.

Unless specifically referred to otherwise, genes are referred to using the nomenclature suggested by Demerec, M., Adelberg, E. A., Clark, A. J. & Hartman, P. E. in "A proposal for a uniform nomenclature in bacterial genetics". *J. Gen. Microbiol* 50, 1-14 (1968).

Figure 1:
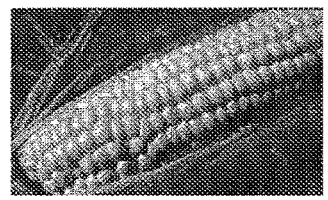
FIG. 1 A schematic depicting pathways in yeast for converting of both corn based starch and plant biomass into ethanol.
Figure 1:
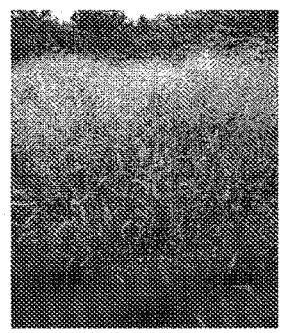
Figure 2:
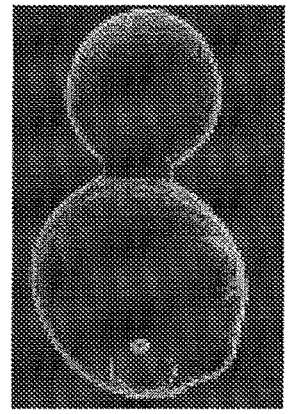
FIG. 2 Schematic showing pathways D-glucose or D-xylose converted into ethanol. A photograph of a budding yeast cell.

The yeast *Saccharomyces cerevisiae* was domesticated centuries ago for the fermentation of sugars into ethanol (See FIGS. 1 and 2). Domestication of yeast has led to the generation of industrial yeast strains that are very efficient at converting D-glucose into ethanol. Significantly, these industrial yeast strains are generally much more ethanol tolerant than most micro-organisms. This process is very efficient when the sugars for yeast growth and/or ethanol production are some of the most abundant hexoses in nature, especially D-glucose, D-fructose, and D-mannose.

In order to make the industrial conversion of cellulose into ethanol a viable commercial enterprise, a great deal of effort is going into streamlining the process of converting of cellulose into fermentable sugars such as glucose. While optimizing the conversion of cellulose into fermentable sugars for the yeast based production of ethanol is important, it is equally important to streamline the production of ethanol from the sugars other than D-glucose present in plant material, especially D-xylose. The most abundant compound in plant material is the glucose polymer cellulose; however, a significant amount of plant biomass is present as the sugar polymer known as xylan (FIG. 1; see, e.g., Warren 1996). In fact, in many sources of cellulose Xylan may make up over 20% of biomass in the polymer. Xylan itself is comprised of chains of the pentose sugar D-xylose. In order to be fermented by yeast such as most industrial and laboratory strains of *S. cerevisiae* xylan, like cellulose, must first be converted into its monomers D-xylose. This already complicated process is further complicated by the presence of D-glucose in the fermentation milieu, as most commercially produced strains of *S. cerevisiae* will not efficiently ferment pentose sugars such as D-xylose and especially not in the presence of D-glucose in the feed stock.

It is widely believed that *S. cerevisiae* cannot ferment D-xylose, in fact it was reported in the 1970's that the yeast *S. cerevisiae* does not utilize D-xylose as a carbon source (Barnett 1976). According to the literature the yeast *Pichia stipitis* does have the ability to ferment D-xylose. Based on this information, several laboratories have attempted to generate yeast strains capable of fermenting D-xylose by expressing the *Pichia* genes necessary for D-xylose utilization in *S. cerevisiae* (see e.g., Kötter and Ciriacy, 1993; Ho et al., 1998; Jin et al., 2003). While improved D-xylose utilization was reported in each case, the efficiency of D-xylose fermentation in the presence of D-glucose varied dramatically. Some factors that may account for this observation include differences in experimental growth and pre-growth conditions, and the levels of heterologous expression of the D-xylose metabolic pathway.

Work from Dr. Ho (Purdue U.) on *Saccharomyces cerevisiae* and Dr. Ingram (U. of Florida) in both gram(−) and gram(+) bacteria have focused on recombinant expression of exogenous genes within the metabolic pathways of other organisms for the catabolism of D-xylose (*Pichia stipitis*) and production of ethanol (from various microbes) respectively.

Without being bound by any theory or hypothesis and by way of explanation and not limitation, there may be several overlooked or at least under-appreciated reasons for these observations. For example, one explanation consisting with the reported results is variability in the exact composition of the D-xylose used in these experiments. Few sugars, purchased from chemical supply companies are actually 'pure'. Most sugars marketed as being pure are actually only about 99 or 98% pure. Typically, the major contaminate in sugars is the extremely abundant sugar D-glucose. Unfortunately for studies on yeast metabolism amount of D-glucose as low as 0.1% D-glucose are known to affect the utilization of a sugar other than D-glucose such as, for example, D-galactose. Accordingly, it is very likely that at least some of the 98-99% pure D-xylose, used in at least some of the published studies was in fact contaminated with D-glucose. And contamination with even scant amounts of D-glucose in studies designed to determine if a given yeast strain can grow on D-xylose could very well have skewed the results observed in these studies.

Contamination of most sugars with D-glucose is a historical problem. For example, the ability to reliably identify yeasts that use D-galactose occurred only after the commercial introduction of D-galactose that includes less than 0.01% D-glucose (Sigma-Aldrich). Unfortunately, D-xylose that is not contaminated with D-glucose is not readily available. Accordingly, reports that some yeast strains lack the ability to grow on D-xylose may be false, and this may account for some of the conflicting reports in the literature.

Figure 3:
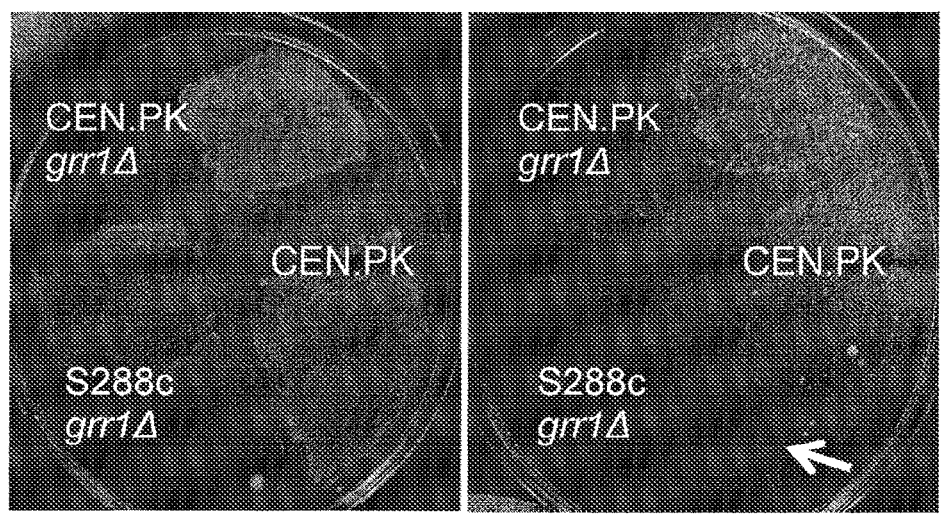
FIG. 3 Plants illustrating growth of some strains of *Saccharomyces* on D-xylose.

Still another explanation for discrepancies reported in the literature regarding xylose fermentation may be due to the diverse genotypic composition of the various laboratory and industrial yeast strains used in these studies. While most laboratory yeast strains were derived from a small number of progenitors (Mortimer and Johnston, 1986), their progeny have developed widely different growth characteristics over time (Winston et al., 1995; van Dijken et al., 2000). In fact, recent papers may suggest to us that at least one strain of S. cerevisiae may grow on D-xylose without genetic modification (see Sedlak and Ho, 2004; FIG. 3; panel marked wild-type; Toivari et al. 2004). The strain MC996A appears to be growing on a commercial grade D-xylose without addition of the *Pichia* D-xylose utilization genes. This strain is a derivative of the CEN.PK family of strains which have been shown to have a very robust genetic background. The apparently rich genetic diversity of these strains enables them to ferment a wide-range of sugars (van Dijkens et al., 2000).

Cellulosic biomass includes multiple sugars, most importantly, D-glucose and D-xylose. However, yeast metabolic physiology is often subject to catabolite repression, the regulated use of D-glucose to the exclusion of many other sugars. Although this had not been demonstrated for D-xylose or D-xylulose, demonstrated herein is that D-xylose and D-xylulose utilization are also under catabolite repression. Accordingly, wild type yeast strains preferentially metabolize glucose. This is an important technical barrier to cellulosic ethanol using most yeast strains. To overcome this barrier to multiple sugar fermentation, one needs to eliminate catabolite repression towards D-xylose.

A yeast strain lacking the capacity to utilize D-glucose can be generated by, for example, creating a strain lacking the hexokinase genes HXK1 and HXK2. It has also found that strains of yeast that harbor mutations in HXK2 and GRR1 also behave like our REG1 mutant (data not shown). Thus, whether analyzing a robust wild-type strain or a strain over-expressing *Pichia* genes of the D-xylose pathway, the presence of D-glucose may prevent D-xylose utilization. Most yeast strains have genes highly related to those necessary for the degradation of D-xylose.

As it stands now even reports that cite the existence of S. cerevisiae that ferment D-xylose admit that they do so inefficiently. For example, Sedlak and Ho (2004), report that very little D-xylose is consumed prior to the utilization of most, if not all, of the D-glucose by a CEN.PK yeast strain that they believes can metabolize D-xylose. The current state of literature clearly illustrates the lack of a robust screen to identify yeast variants that can reliably grow on pentoses such as D-xylose. Assuming that pathways for the fermentation of D-xylose exist in S. cerevisiae it would be much easier to study, improve, and augment these pathways once a robust screen for them is created.

Figure 4:
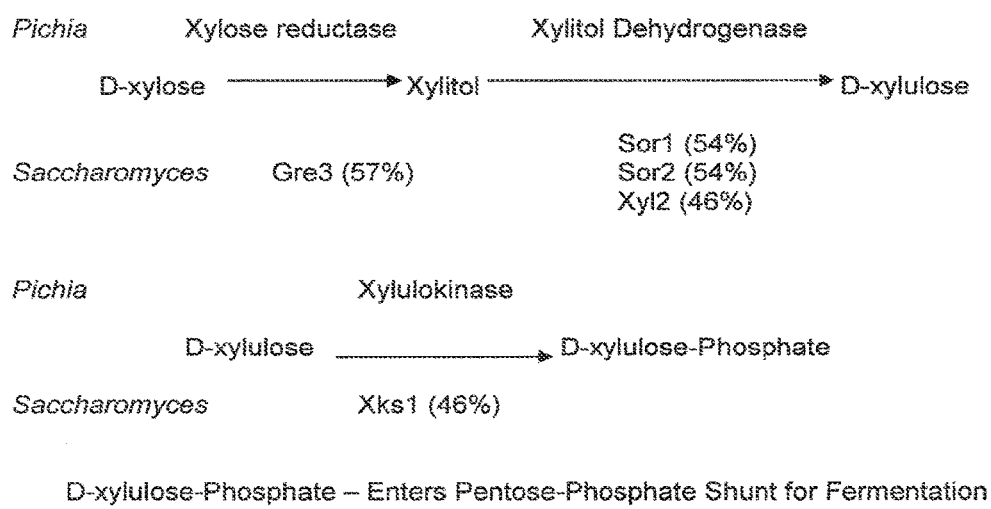
FIG. 4 Proposed pathways for fermentation of D-xylose by brewer's yeast.

Referring now to FIG. 3, Panel A. Results disclosed herein illustrate that it is possible to screen for and isolate a spontaneous mutant of CEN.PK that can grown on xylose. This result is consistent with the analysis of the complete sequence of the *Saccharomyces* genome which illustrates that close homologs for each enzyme required for D-xylose fermentation are present in *Saccharomyces* (FIG. 4).

Referring to FIG. 3. Growth of S288c and aCEN.PK derivative on D-xylose. In FIG. 3 Panel A the cells were replica-plated onto YP plus 2% D-xylose media and incubated at 30° C. for 4 days. In FIG. 3 Panel B, the cells were replica-plated onto YP plus 2% D-xylose/0.1% 2-deoxyglucose and incubated at 30° C. for 10 days. The arrow in Panel B points to colonies arising from spontaneous mutants of the CEN.PK growing in the presence of 2-deoxyglucose.

Yeast cells are highly efficient at fermenting D-glucose, D-fructose, and D-mannose; furthermore, yeast ferment these sugars to the exclusion of many other carbon sources, a phenomenon known as catabolite repression (reviewed in Gancedo 1998). Indeed, virtually all strains of S. cerevisiae studied so far rely solely on D-glucose, D-fructose, and/or D-mannose for energy until these sugars are completely or nearly completely eliminated from the environment. For example, if only trace amounts of D-glucose (<1%) contaminate D-galactose, yeast will not ferment D-galactose until all D-glucose present is exhausted. The conflicting reports in the literature concerning D-xylose utilization by S. cerevisiae may be due to contamination of the growth media with D-glucose which causes catabolite repression.

Mutations in several genes have been shown to relieve catabolite repression in laboratory strains in the context of maltose, sucrose, and D-galactose based fermentations. Genes thought to be involved in catabolite repression include GRR1, REG1, and HXK2 (reviewed in Gancedo, 1998). Loss of anyone of these genes within certain laboratory strains may enable some laboratory strains co-fermentation of D-glucose along with other hexoses such as D-galactose or sucrose (Bailey and Woodward, 1984).

One test of the ability of yeast cells derived from laboratory yeast to utilize some secondary carbon sources in the presence of D-glucose is to measure the ability of cells to grow in the presence of a secondary carbon source and a small amount of 2-deoxy-glucose. 2-deoxy-glucose is a non-metabolizable derivative of D-glucose that is reported to exhibit glucose repression against hexose sugars such as D-galactose, maltose, and sucrose in certain laboratory strains. This phenomenon is demonstrated with D-galactose (Bailey et al., 1982; Bailey and Woodward, 1984). Yeast cells exposed to 2-deoxy-glucose, which are both catabolite repression competent and capable of fermenting D-galactose, maltose, or sucrose, are believed to be unable to utilize alternative carbon sources in the presence of 2-deoxyglucose and these strains are unable to metabolize 2-deoxyglucose. These conditions reportedly result in cell death; however, the exact cause of death in yeast cells exposed to 2-deoxy-glucose is still unclear (Raiser et al. 2008).

Glucose repression describes a phenomenon in yeast whereby D-glucose must be depleted from the media prior to the utilization of most other carbon sources. A well studied regulator of glucose repression is the Mig1 transcription factor which is thought to act as a transcriptional repressor of genes involved in the utilization of alternative carbon sources; however, it is also reported that the loss of MIG1 does not make cells resistant to 2-deoxy-glucose (Schüller, 2003). As mentioned above, loss of GRR1, REG1, or HXK2 makes cells resistant to 2-deoxy-glucose (Gancedo 1998). While Reg1 is a PP1 protein phosphatase subunit that is believed to regulate Mig1 by bringing a PP1 complex to Mig1, the precise mechanisms by which the other proteins are necessary to achieve glucose repression are less clear. Microarray analysis also indicates that Mig1 affects only a subset of the processes regulated by Grr1 and Hxk2 (Westergaard et al. 2006). The experimental results proteomics analyses performed and reported on herein suggest that a large post-transcriptional component to the regulation of catabolite repression is unrecognized.

Figure 6:
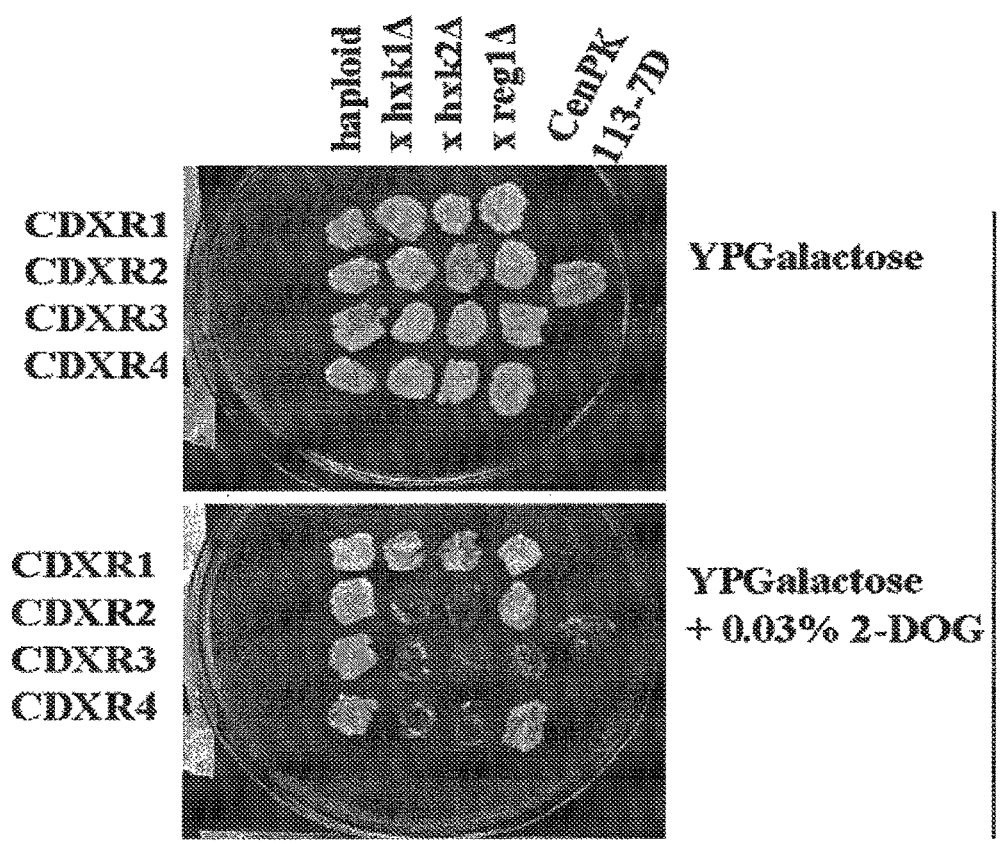
FIG. 6 Photograph of plants showing the results of complementation analysis of 2-deoxy-glucose resistant derivatives of CEN.PK.

Spontaneous mutations in CEN.PK isolated in the screen mention in 1 exhibit an inactivation in the REG1 locus (FIG. 6). Furthermore targeted disruption of REG1 or two other genes known to have similar mutant phenotypes when lost, GRR1 and HXK2, also gained the ability to grow on this medium. Targeted disruption of REG1, GRR1 or HXK2 may be created by PCR-mediated gene disruption. These experiments can be carried out by designing primers which are identical to the 5' and 3' segments of DNA at a particular gene locus. Using the nat1 gene from Streptomyces nourseothricii, which confers resistance to the aminoglycoside antibiotic nourseothricin, any of the genes listed above can be deleted by transforming yeast using the lithium acetate transformation method. In a haploid strain, disruption of a single allele is sufficient to allow growth on YP media supplemented with L-glutamine, 2% D-xylose and 0.1% 2-deoxy-glucose. However, different yeast strains are differentially sensitive to different concentrations of 2-deoxy-glucose.

Most industrial yeast strains are diploid. Accordingly, transformation in these strains only ensures deletion of a single allele. Surprisingly, we have found the reproducible loss of the other copy at the same gene locus of a diploid or any higher ploidy yeast can be accomplished by plating the heterozygotic strain on media containing 2-deoxy-glucose and a secondary sugar serving as the principle carbon source including but not limited to sugars such as maltose, D-galactose, sucrose, D-xylose or D-xylulose.

Figure 5:
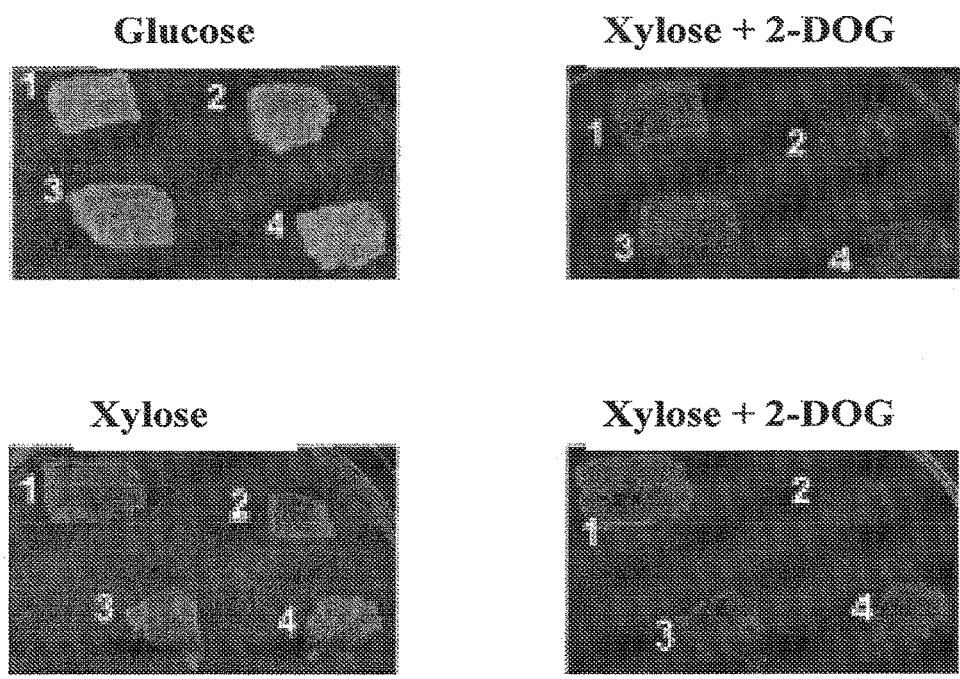
FIG. 5 Photograph of plates showing the growth of mutant yeast colonies of CEN.PK growing on YP plus 2% D-xylose.

Referring now to FIGS. 3 and 5. This phenomenon was also demonstrated in the context of D-xylose. As shown in FIG. 3, when an S288c grr1Δ strain, a wild-type CEN.PK strain and a CEN.PK grr1Δ strain were plated onto media containing 2% D-xylose, growth could be detected for all three strains. However, only the CEN.PK grr1Δ strain shows growth on media containing 2% D-xylose and 0.1% 2-deoxy-glucose (FIG. 3). Over time within the patch of cells from the CEN.PK strain, isolated colonies began to emerge after 10-15 days.

After about 21 days, these colonies become large enough to be physically manipulated. These isolated colonies are spontaneous mutants of the CEN.PK parent strain that have gained the ability to grow on D-xylose in the presence of 2-deoxy-glucose (see below). This phenomenon is not observed with the S288c grr1Δ derivative. These results illustrate that in contrast to CEN.PK cells, even upon deletion of the GRR1 gene, S288c cells are incapable of growing on D-xylose in the presence of 2-deoxy-glucose. The inability of 2-deoxy-glucose resistant/D-xylose utilizing mutants to develop in S288c suggests that the small amount of growth seen with S288c may be due to the utilization of contaminating amounts of glucose within the D-xylose.

Two representative haploid strains Saccharomyces cerevisiae isolated the screen disclosed herein and those that grow on D-xylose in the presence of 2-deoxy-glucose CDXR2 and JH015 were deposited with the American Type Culture Collection on Feb. 25, 2009 and have been assigned accession numbers PTA-9849 and PTA-9850, respectfully. Under terms of the Budapest Treaty on deposits of biological materials these strains will be made available to public once a patent issues on this invention.

The conversion of yeast's cellular metabolism from the utilization of the preferred sugars to non-preferred sugars (e.g. D-galactose and likely D-xylose) may take hours. This lag occurs even in yeast cells that have been engineered to over-express the enzymes necessary for D-xylose breakdown. It appears that in both industrial and laboratory yeast strains that utilize a mixture of sugars is the metabolism of D-xylose is very inefficient until the mixture is almost completely devoid of D-glucose.

Figure 9:
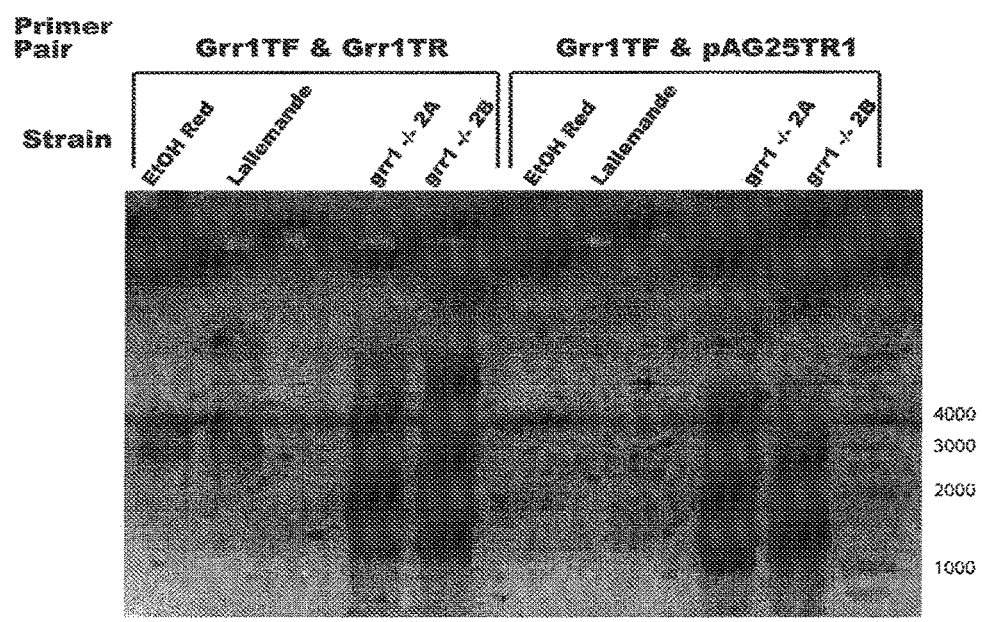
FIG. 9 Cell showing PCR analysis is performed to check for the identification of deletion of the GRR1 gene.

Referring now to FIG. 9. Diploid industrial yeast strained selected for by their ability to grow on Xylose in the presence of 2-dexoy-glucose were analyzed using PCR. Three Grr1Tf and Grr1TF primer pairs should produce a PCR product of 3810 bp if GRR1 is intact; if GRR1 is disrupted the PCR product should be 1400 bp. The Grr1Tf & pAG25TR1 primer pairs should produce no PCR product if GRR1 is intact and a PCR product of ~1200 bp if GRR1 has been replaced by the nat1 gene. The PCR analysis proves that in the grr1-/-2A and grr1-/-2B strains which are derivatives of Fermentis Ethanol Red, both GRR1 genes have been displaced with the nat1 gene. Note that RC4 is a haploid S288C derivative with grr1::NAT1. Two previous PCR reactions (Oct. 18, 2004 and Dec. 10, 2009) returned the same product as that observed for the grr1-/- strains in this PCR reaction.

Figure 10:
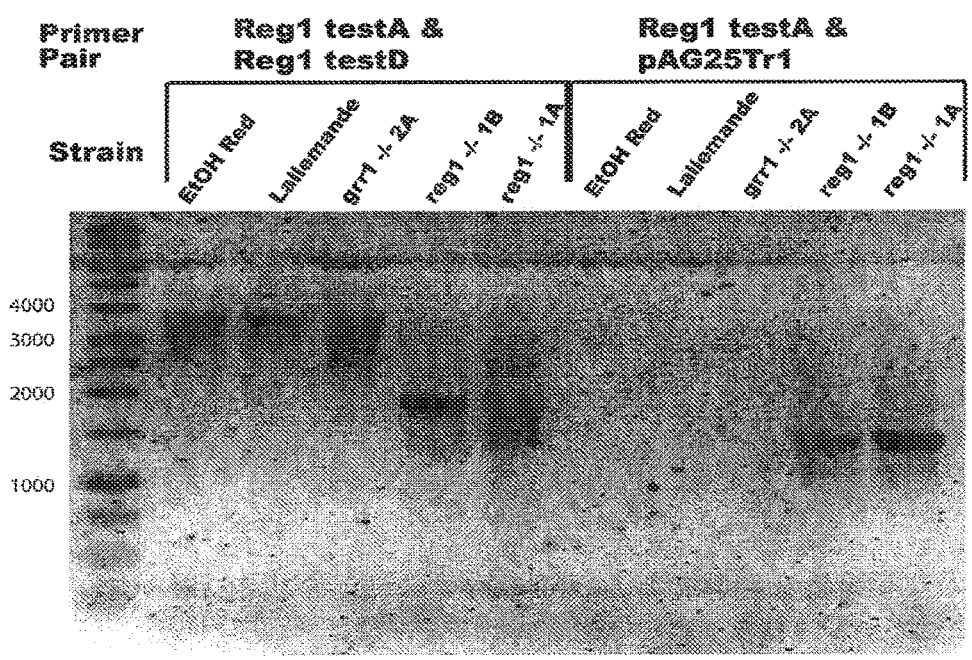
FIG. 10 Cell showing PCR analysis performed to check for deletion of the REG1 gene.

Referring now to FIG. 10. A similar analysis of the diploid industrial strains was carried out to look for changes in the Reg 1 gene. The Reg1 testA & Reg1 test ID primer pairs should produce a PCT product of ~3600 bp if REG 1 is intact; if disrupted the PCR product should be ~1800 bp. The Reg1 testA & pAG25TR1 primer pairs should produce no PCR product if REG 1 is intact and a PCR product of ~1500 bp if REG 1 has been replaced by the nat1 gene. The PCR above proves that in the reg1-/-1A and reg 1-/-1B strains which are derivatives of Fermentis Ethanol Red, both REG1 genes have been displaced with the nat1 gene. It is also proof that even in strains harboring the Nat1 gene, like grr1-/-2A, no PCR product is made with the REG1 testA and pAG25T41 primers.

The strength of the repressing effect of D-glucose is illustrated in Table 1 which includes the levels of a select group of transcripts that are regulated by D-xylose (Jin et al. 2004) as well as by different concentrations of D-glucose (Yin et al. 2003). The regulation of these transcripts in cells mutant for GRR1 and HXK2 while growing in 2% D-glucose as compared to wild-type cells has also been included (Westergaard et al. 2006). As can be seen in Table 1, even a constant level of low D-glucose (0.01%) causes catabolite repression. For example, the abundance of the FBP1 transcript remains relatively constant from 0.01%-1% D-glucose while it is highly induced by growth on 2% D-xylose or in cells lacking GRR1. Eliminating catabolite repression should be of use even if it is possible to process a mixed sugar feed stock to reduce the level of D-glucose mixed sugar feed stocks below those levels that induce catabolite repression, because having to process mixed sugar stocks to substantially deplete them of D-glucose is time consuming and expensive.

TABLE 1

Expression ratios of genes involved in sugar metabolism.

| | | mRNA microarray Analysis | | | | 2.0% D-glucose | | Protein Analysis |
|---|---|---|---|---|---|---|---|---|
| | | D-glucose | | | D-xylose | | | |
| ORF | Gene | 0.01% | 0.1% | 1.0% | 2.0% | hxk2Δ | grr1Δ | grr1Δ |
| Gluconeogenesis Genes | | | | | | | | |
| YLR377c | FBP1 | 0.31 | 0.26 | 0.30 | 5.56 | 2.30 | 136.60 | ND |
| YHR094c | HXT1 | 3.52 | 5.18 | 8.97 | 0.31 | 0.15 | 0.01 | 1.00 |
| YKL085w | MDH1 | 0.7 | 0.67 | 0.33 | 2.04 | 2.36 | 2.24 | 0.47 |
| YMR145c | NDE1 | | | | 1.52 | 2.10 | 1.46 | 3.22 |
| YML120c | NDI1 | | | | 2.38 | 4.05 | 3.75 | 0.35 |
| YKR097w | PCK1 | 0.12 | 0.21 | 0.17 | 3.00 | ND | 38.64 | ND |
| YKL148c | SDH1 | 0.76 | 0.66 | 0.46 | 2.90 | 4.61 | 3.94 | ND |
| YFR053c | HXK1 | 3.11 | 5.00 | 1.21 | 7.81 | 13.38 | 8.28 | 1.40 |
| YDR342- | HXT6/7 | 8.00 | 11.00 | 3.50 | 7.20 | 6.40 | 4.62 | .35 |
| YHR104w | GRE3 | | | | | | 0.78 | 16.36 |

As disclosed herein, a proteomic analysis of cells lacking GRR1 was carried out and an analysis of this data illustrates at least the following two points. First, transcript levels do not always provide an accurate picture of the proteome (Table 1). For example, while the transcripts from the genes HXT1 and HXT7 are decreased and increased respectively, the corresponding proteins behave quite differently, Hxt1 protein levels remain unchanged when comparing a wild-type strain to a grr1Δ strain while the Hxt7 protein is reduced in a grr1Δ. These results indicate that one must exercise caution when interpreting mRNA microarray data in the absence of proteomic data. This is highly relevant here because Hxt7 has been proposed to be an important transporter of D-xylose.

Second, this proteomic data indicates that the Gre3 protein is elevated over 16× in a grr1Δ mutant strain. GRE3 encodes a homolog of the *Pichia* xylose reductase which carries out the first step in D-xylose degradation. Furthermore, the increase in Gre3 occurs in the absence of transcriptional induction of the GRE3 gene and can only be seen by direct detection of the protein in our experiments. Thus the absence of GRR1 further drives a cell toward utilization of D-xylose. These results indicate that loss of GRR1, HXK2, and most likely REG1 may provide very similar, if not entirely overlapping responses.

Microarray analysis provides a means to monitor global transcriptional changes in an unbiased fashion. An inherent assumption in microarray experiments is that differences in mRNA levels reflect differences in protein levels. However, not all protein changes in protein activity or even levels require a change in transcriptional controls. For example, post-translationally mediated events may bring about dramatic proteomic changes that would be "invisible" in a microarray analysis. Fortunately, a combination of microarray analysis and proteomic analyses can be used to distinguish transcriptional from post transcriptional regulatory events responsible for changes in the abundance of specific proteins.

Quantitation data on about 1,200 proteins out of 2580 proteins detected was compiled (Data now shown), a result typical for this method (de Godoy et al. 2006). These proteomic data were coupled to a microarray analysis using the strains and media conditions described above (for a GRR1 mutant) as well as published microarray analyses comparing wild-type cells to grr1 mutants and to other catabolite repression mutants (Kodama et al., 2002; Kaniak et al., 2004; Westergaard et al., 2004). Analysis of these data sets revealed three distinct patterns of regulation influenced by GRR1 (Data now shown). First, genes whose mRNA abundances correlate with protein product abundances were identified. Second, genes where product abundance differences occur in the absence of mRNA changes were found. Genes were also identified in which their mRNA abundance changes without concomitant changes in product abundance. These results indicate that under the proper conditions these techniques can be used to study the proteome of various active metabolic pathways proteomically.

TABLE 2

| ORF Name | Gene Name | Function | Relatives |
|---|---|---|---|
| YLR063w | None | Unknown | None |
| YMR167w | MLH1 | DNA Repair | PMS1, MHL2, MLH3 |
| YPL176c | TRE1 | Ub/RSP5 | TRE2 |
| YPL123c | RNY1 | RNase | None |
| YPL121c | MEI5 | DNA Repair | None |
| YBR242w | None | Unknown | YGL101w |
| YDR422c | SIP1 | Metabolism | GAL83, SIP2 |
| YHR012w | VPS29 | Retromer Com. | YHR012w |
| YHR103w | SBE22 | Cell Wall | SBE2 |
| YHR154w | RTT107 | DNA Repair | None |
| YCL048w | SPS22 | Cell Wall | SBE2, PST1, ECM33 |
| YLR133w | CKI1 | PL Synthesis | EKI1 |
| YOR138c | RUP1 | UB/RSP5 | None |
| YOR177c | MPC54 | Unknown | None |
| YDR269c | CCC2 o/l | Transport CU++ | PCA1 |
| YIL064w | None | Unknown | None |
| YOL101c | IZH4 | Transport Zn++ | IZH1, IZH2 |
| YML124c | TUB3 | MT | TUB1 |
| YMR116c | ASC1 | Metabolism | None |
| YDR028c | REG1 | Metabolism | REG2 |
| YDR074w | TPS2 | Metabolism | None |
| YDL088c | ASM4 | Nuclear Pore | NUP53 |
| YGR271w | SLH1 | Unknown | None |

EXPERIMENTAL

1. Screening for Catabolite Derepressed Haploid Spontaneous Mutants of *S. cerevisiae*

The following experiments were carried out to examine the growth of yeast cells on 2-deoxy-glucose. Wild type yeast strains were plated onto solid media YP including 2 wt. % xylose and 0.1 wt./% 2-deoxy-glucose. However, no yeast cell growth was seen.

Next 0.5 wt. % L-glutamine was added to otherwise identical media and growth was found after several days of incubation. However, as can be seen in FIG. 3, (Panel B) the cells did not readily grow on this media. Only after incubation for three weeks did Cen.PK derivatives, but not cells derived from other yeast strains, unexpectedly gain the ability to grow on xylose in the presence of 2-deoxy-glucose. These spontaneous mutants, eventually, formed colonies which appear to have arisen from a single cell. While these colonies were derived from spontaneous mutagenesis, classic chemical mutagens or irradiation could enhance this process.

2 Replating of Haploid Mutants

Cells from four of the 2-deoxy-glucose resistant/D-xylose utilizing CEN.PK colonies were isolated and set aside for further study. Referring now to FIG. 5, these mutant CEN.PK strains grow on D-glucose and D-xylose and, when transferred to D-xylose plus 2-deoxy-glucose (DOG) media, produce a robust patch within two days.

3. Complementation Analysis

The 2-deoxy-glucose resistant Cen.PK derivative, strains that were isolated were mated to specific strains from the yeast knockout collection (Open Biosystems). All four 2-deoxy-glucose resistant mutant strains also grew on media containing 2% galactose and 0.03% 2-deoxy-glucose. Thus, since S288c derived cells do not grow on D-xylose, complementation tests were performed on media containing D-galactose and 2-deoxy-glucose. The analysis demonstrated that the 2-deoxy-glucose phenotype of CDXR2 and CDXR4 is not complemented by a mutation in REG1 indicating that CDXR2 and CDXR4 contain mutant alleles of REG1. There may also be still unidentified changes in these strains responsible for these unusual phenotype.

4. Screening and Targeted Approaches for Obtaining Derepressed Diploid Industrial Yeast Strains Using a similar approach to that used with haploid laboratory strains it should be possible to screen for and isolate modified versions of the industrial diploid strain Fermentis Ethanol Red that spontaneously gained the ability to grow robustly on a mixture of D-xylose and D-xylulose in the presence of 2-deoxy-glucose.

Some industrial diploid strains, such as Fermentis Ethanol Red, are heterothallic and can be made and sustained as a haploid by the standard laboratory practices of sporulation and tetrad dissection. Converting an industrial diploid strain to a haploid will increase that strain's ability to acquire the properties necessary to grow robustly on a mixture of D-xylose in the presence of 2-deoxy-glucose because only a single copy of a gene imparting glucose repression needs to be disrupted.

Derepressed industrial diploid strains can also be obtained by targeted gene disruption followed by selection for loss of the second copy of a gene. For example, strain GX1 (grr1−/−) was created by replacing one of the two genomic copies of the GRR1 gene with the nourseothricin N-acetyltransferase gene (NAT1) gene, which confers resistance to the aminoglycoside nourseothricin, in the Fermentis Ethanol Red strain. By plating the heterozygotic strain on media containing 2-deoxy-glucose and a secondary sugar serving as the principle carbon source including but not limited to sugars such as maltose, D-galactose, sucrose, D-xylose or D-xylulose, a strain lacking both copies of the GRR1 gene was obtained.

Figure 7:
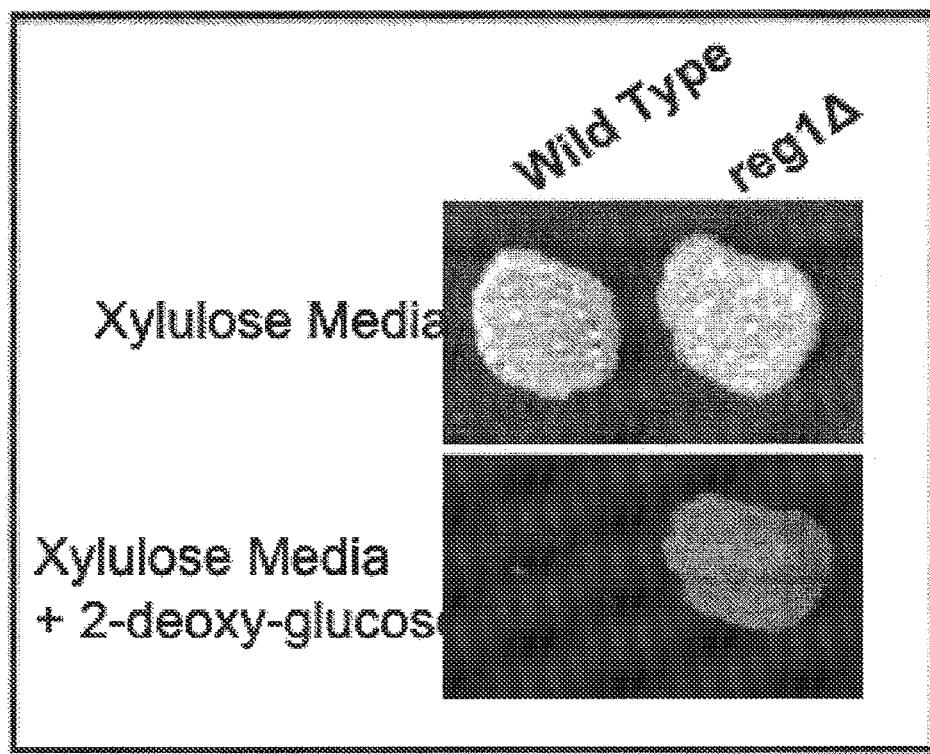
FIG. 7 Photographs of plants illustrated by yeast growing on a D-xylulose, D-xylose mixture in the presence of 2-deoxy-glucose.

Referring now to FIG. 7. Industrial diploid, wild type (Fermentis Ethanol Red) and reg1Δ (Fermentis Ethanol Red derivative) were grown on YPD plates for two days and then replica-plated onto YP plus 0.4% Xylulose/3.6% Xylose/ (top panel) or YP plus 0.4% Xylulose/3.6% Xylose plus 0.1% 2-deoxy-glucose and grown at 30° C. for 3 days.

Figure 8:
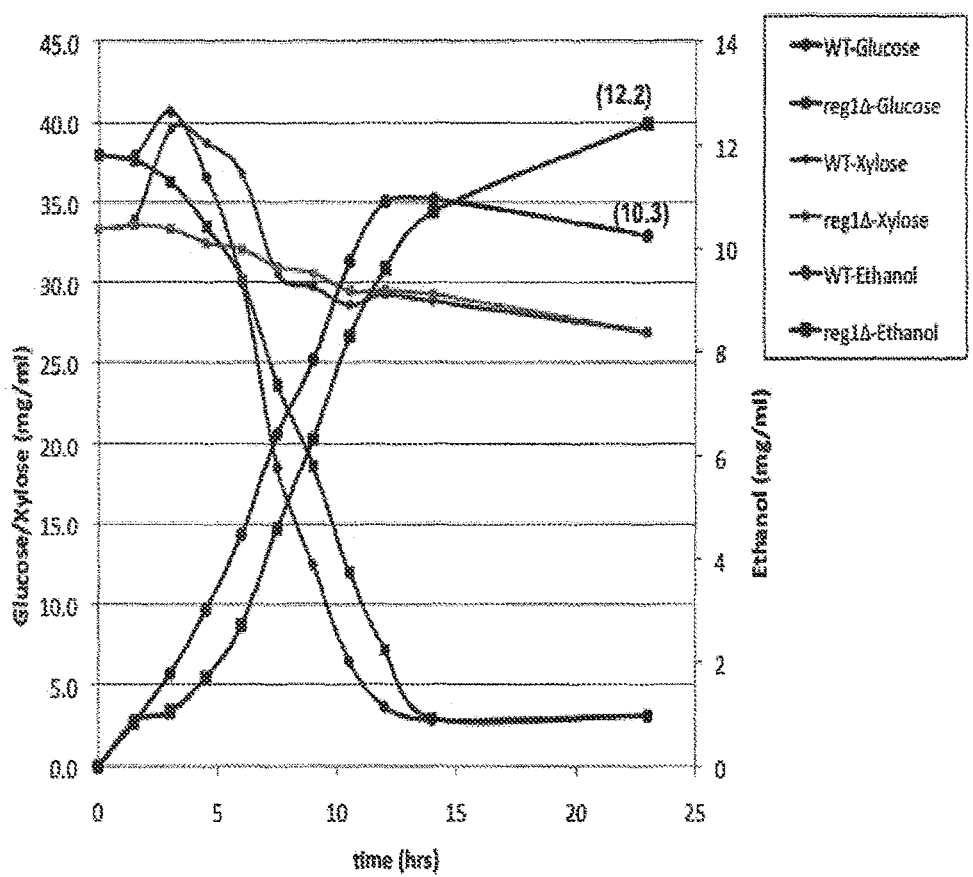
FIG. 8 Graphic illustration of the fermentation of corn cob hydrolysate into ethanol by various strains of industrial yeast.

5. Growth of Mutant Industrial Diploid Yeast Strains on Corn Cob Hydrolysate The ability of the mutant diploid industrial to grow on a mixture of glucose and xylose was tested. The industrial diploid strains, wild type (Fermentis Ethanol Red) and reg1Δ (Fermentis Ethanol Red derivative) strains were inoculated into 50 ml of corn cob hydrolysate at a starting density of $1\times10^7$ cells/ml. Cultures were shaken at 30° C. and samples were withdrawn at the indicated times. The concentrations of glucose, xylose and ethanol were analyzed by refractive index. Referring now to FIG. 8. The mutant strain also converts a greater percentage of sugar into ethanol (~11%) in a cellulosic mixture derived from corn cobs that includes both D-glucose and D-xylose.

Figure 11:
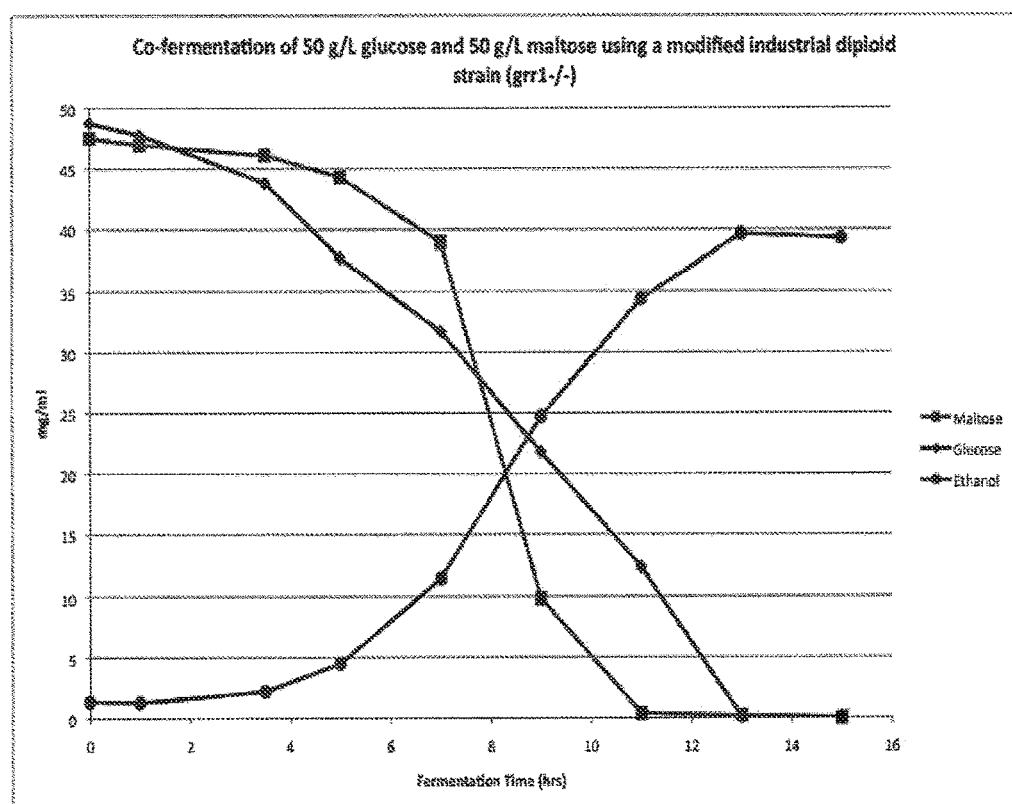
FIG. 11 Graphic illustrating co-fermentation of maltose and D-glucose by GX1.

6. Growth of Mutant Industrial Diploid Yeast Strains on a Mixed Sugar Source Including Both Glucose and Maltose Industrial diploid strains, wild type (Fermentis Ethanol Red) and grr1−/− (GX1) (a Fermentis Ethanol Red derivative), were inoculated into 50 ml of media containing 10 g/L yeast extract, 20 g/L peptone, 50 g/L glucose and 50 g/L maltose at a starting density of $1\times10^7$ cells/ml. Cultures were shaken at 30° C. and samples were withdrawn at the indicated times. The concentrations of glucose, xylose and ethanol were analyzed by refractive index. As illustrated in FIG. 11, this strain also utilizes maltose more quickly than D-glucose when provided both sugars simultaneously.

7. PCR-Mediated Conformation of the GRR1 and REG1 Disruption

The conditions used for the PCR analysis of the GRR1 gene are as follows.

| PCR Mix | RC4 Program |
|---|---|
| 5 ul 10X Thermo Pol Rxn Buffer | 94 C. - 1 min |
| 39 ul Water | 94 C. - 50 sec\| |
| 1 ul dNTPs (10 mM each, initial [ ]) | 56 C. - 1 min \| 30X |
| 1.5 ul each primer (10 mM, initial [ ]) | 72 C. - 3 min \| |
| 1 ul genomic DNA | |
| 1 ul Taq (NEB) | |

The following DNA primers were used in the analysis of GRR1.

```
Grr1TfF =                          SEQ. ID NO. 1
5' GAAGCCCAAAAATTAAGGCATTGCA

Grr1TR =                           SEQ. ID NO. 2
5' TTTGAAACTGTGTATAGAATGTTTCGC pAG25Tr1 =                         SEQ. ID NO. 3
5' ATTACTTTCTGCGCACTTAACTTCG
```

The results of these reactions are illustrated in the gel shown in FIG. 9.

8. PCR Analysis of REG1 Disruption

The conditions used for the PCR analysis of the REG1 gene are as follows.

| PCR Mix | RC4 Program |
| --- | --- |
| 5 ul 10X Thermo Pol Rxn Buffer | 94 C. - 1 min |
| 39 ul Water | 94 C. - 50 sec\| |
| 1 ul dNTPs (10 mM each, initial [ ]) | 56 C. - 1 min \| 30X |
| 1.5 ul each primer (10 mM, initial [ ]) | 72 C. - 3 min \| |
| 1 ul genomic DNA | |
| ul Taq (NEB) | |

The following DNA primers were used in the analysis of Reg1.

```
Reg1 testA =                         SEQ. ID NO. 4
5' AGAATATACCATATAGGAGACGCGA Reg1 testD =                         SEQ. ID NO. 5
5' TACGACTATGGAAGCTCAAGAAGTT pAG2tTr1 =                           SEQ. ID NO. 6
5' ATTACTTTCTGCGCACTTAACTTCG
```

The results of these reactions are illustrated in the gel shown in FIG. 10.

9. Comparison of Yeast Genes Thought to be Involved in Carbon Metabolism

Concerted measurements of gene and protein expression were performed on a S288c derived strain grr1Δ strain. This strain was constructed using the same methods described in experiment 4. Referring now to table 1. Even within this selected list of key carbon metabolism genes, it can be seen that there is great similarity in the transcriptional response of cells growing on D-xylose and those growing on D-glucose but lacking either HXK2 or GRR1, two key catabolite repression genes.

10. Identification of Various Single Gene Deletion Strains which are Resistant to 2-Deoxy-Glucose A collection of viable yeast deletion mutants was screened to identify those resistant to 2-deoxy-glucose. This experiment was performed by growing cells from the Open Biosystem yeast gene deletion collection on YP media containing 2% D-galactose and 0.03% 2-deoxy-glucose and observing for growth after a 3 day incubation at 30° C. D-galactose was used since this strain does not grow on D-xylose under any condition we have tested. This analysis allows us to increase the list of mutations that might lead to fermentation of D-xylose in the presence of D-glucose. The results are presented in table 2.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

REFERENCES

Bailey, R. B., Benitez, T., and Woodard, A. 1982. *Saccharomyces cerevisiae* mutants resistant to catabolite repression: Use in cheese whey hydrolysate fermentation. *Appl. Environ. Microbiol.* 44: 6310639.

Bailey, R. B. and Woodward, A. 1984. Isolation and characterization of a pleiotropic glucose repression resistant mutant of *Saccharomyces cerevisiae. Mol. Gen. Genet.* 193: 507-512.

Barnett, J. A. 1976. The utilization of sugars by yeast. *Adv. Carbohydr. Chem. Biochem.* 32: 126-228.

De Godoy, L. M. F., Olsen, J. V., de Souza, G. A., Li, G., Mortensen, P., and Mann, M. 2006. Status of complete proteome analysis by mass spectrometry: SILAC labeled yeast as a model system. Genome Biol. 7:R50.1-R50.15.

Gancedo, J. M. 1998. Yeast catabolite repression. *Microbiol. Mol. Biol. Rev.* 62: 334-361.

Gavin, A.-C., Aloy, P., Grandi, P., Krause, R., Boesche, M., et al. 2006. Proteome survey reveals modularity of the yeast cell machinery. *Nature* 440: 631-636.

Goldstein, A. I. and McCusker, J. H. 1999. Three new dominant resistance cassettes for gene disruption in *Saccharomyces cerevisiae. Yeast* 15: 1541-1553.

Ho, N. W. Y., Chen, Z., and Brainard, A. P. 1998. Genetically engineered *Saccharomyces* yeast capable of effective co-fermentation of glucose and xylose. *Applied Env. Microbiol* 64: 1852-1859.

Jin, Y.-S., Laplaza, J. M., and Jeffries, T. W. 2004. *Saccharomyces cerevisiae* engineered for xylose metabolism exhibits a respiratory response. *Applied Env. Microbiol.* 70: 6815-6825.

Kaniak, A., Xue, Z., Macool, D., Kim, J.-H., and Johnston, M. 2004. Regulatory network connecting two glucose signal transduction pathways in *Saccharomyces cerevisiae. Euk. Cell* 3: 221-231.

Keller, A., Nesvizhskii, A. I., Kolker, E., and Aebersold, R. 2003. Empirical statistical model to estimate the accuracy of peptide identifications made by MS/MS and database search. *Anal. Chem.* 74: 5383-5392.

Kodama, Y., Omura, F., Takahashi, K., Shirahige, K., and Ashikari, T. 2002. Genomewide expression analysis of genes affected by amino acid sensor Ssy1p in *Saccharomyces cerevisiae. Curr. Genet.* 41: 63-72.

Kötter, P. and Ciriacy, M. 1993. Xylose fermentation by *Saccharomyces cerevisiae. Appl. Microbiol. Biotechnol.* 38: 776-783.

Li, X., Zhang, H., Ranish, J. A., and Aebersold, R. 2003. Automated statistical analysis of protein abundance ratios from data generated by stable-isotope dilution and tandem mass spectrometry. *Anal. Chem.* 75: 6648-6657.

Lynd, L. R., Weimer, P. J., van Zyl, W. H., and Pretorius, I. S. 2002. Microbial cellulose utilization: Fundamentals and biotechnology. *Microbiol. Mol. Biol. Rev* 66: 506-577.

Mathias, N., Johnson, S. L., Winey, M., Adams, A. E. M., Goetsch, L., Pringle, J. R., Byers, B., and Goebl, M G. 1996. Cdc53p acts in concert with Cdc4p and Cdc34p to control the G1-to-S-phase transition and identifies a conserved family of proteins. *Mol. Cell. Biol.* 16: 6634-6643.

Mortimer, R. K. and Johnston, J. R. 1986. Genealogy of principal strains of the yeast genetic stock center. *Genetics* 113: 35-43.

Nesvizhskii, A. I., Keller, A., Kolker, E., and Aebersold, R. 2003. A statistical model for identifying proteins by tandem mass spectrometry. *Anal. Chem.* 75: 4646-4658.

Neigeborn, L. and Carlson, M. Mutations causing constitutive invertase synthesis in yeast: Genetic interactions with snf mutations. *Genetics* 115: 247-253.

Ong, S. F., Blagoev, B., Kratchmarova, I., Kristensen, D. B., Steen, H., Pandey, A., Mann, M. 2002. Stable isotope labeling by amino acids in cell culture, SILAC, as a simple and accurate approach to expression proteomics. *Mol. Cell. Proteomics* 1: 376-386.

Phaff, H. J., Starmer, W. T., and Kurtzman, C. P. 1999. *Pichia lachancei* sp. November, associate3d with several Hawaiian plant species. *Int J. Syst. Bacteriol.* 49: 1295-1299.

Ralser, M., Wamelink, M. M., Struys, E. A., Joppich, C., Krobitsch, S., Jakobs, C., and Lehrach, H. 2008. A catabolic block does not sufficiently explain how 2-deoxy-glucose inhibits cell growth. *Proc. Natl. Acad. Sci. USA* 105: 17807-17811.

Schüller, H.-J. 2003. Transcriptional control of nonfermentative metabolism in the yeast *Saccharomyces cerevisiae* *Curr. Genet.* 43: 139-160.

Schulte, F., Wieczorke, R., Hollenberg, C. P., and Boles, E. The HTR1 gene is a dominant negative mutant allele of MTH1 and blocks Snf3- and Rgt2-dependent glucose signaling in yeast. *J. Bac.* 182: 540-542.

Sedlak, M. and Ho, N. W. Y. 2004. Characterization of the effectiveness of hexose transporters for transporting xylose during glucose and xylose co-fermentation by a recombinant *Saccharomyces* yeast. *Yeast* 21: 671-684.

Toivari, M. H., Salusjärvi, L., Ruohonen, L., and Penttilä, M. 2004. Endogenous xylose pathway in *Saccharomyces cerevisiae*. *Appl. Environ. Microbiol.* 70: 3681-3686.

Tu, J. and Carlson, M. 1994. The GLC7 type 1 protein phosphatase is required for glucose repression in *Saccharomyces cerevisiae*. *Mol. Cell. Biol.* 14: 6789-6796.

Van Dijken, J. P., Bauer, J., Brambilla, L., Duboc, P. et al. 2000. An interlaboratory comparison of physiological and genetic properties of four *Saccharomyces cerevisiae* strains. *Enz. Microb. Tech.* 26: 706-714.

Van Zyl, C., Prior, B. A., Kilian, S. G., and Brandt, E. V. 1993. Role of D-ribose as a co-metabolite in D-xylose metabolism by *Saccharomyces cerevisiae*. *Appl. Environ. Microbiol.* 59: 1487-1494.

Warren, R. A. J. 1996. Microbial hydrolysis of polysaccharides. *Annu Rev. Microbiol.* 50: 183-212.

Washburn, M. P., Wolters, D., Yates, J. R., III. 2001. Large-scale analysis of the yeast proteome by multidimensional protein identification technology. *Nat. Biotech.* 19: 242-247.

Westergaard, S. L., Bro, C., Olsson, L., and Nielsen, J. 2004. Elucidation of the role of Grr1p in glucose sensing by *Saccharomyces cerevisiae* through genomewide transcriptional analysis. *FEMS Yeast Res.* 5: 193-204.

Westergaard, S. L., Oliveira, A. P., Bro, C., Olsson, L., and Nielsen, J. 2006. A systems biology approach to study glucose repression in the yeast *Saccharomyces cerevisiae*. *Biotechnol. Bioeng.* 1: 134-145.

Winston, F., Dollard, C., AND Ricupero-Hovasse, S. L. 1995. Construction of a set of convenient *Saccharomyces cerevisiae* strains that are isogenic to S288C. *Yeast* 11:53-55.

Yin, Z., Wilson, S., Hauser, N. C., Tournu, H., Hoheisel, J. D., and Brown, A. J. P. 2003. Glucose triggers different global responses in yeast, depending on the strength of the signal, and transiently stabilizes ribosomal protein mRNAs. *Mol. Microbiol.* 48: 713-724.

---

The invention claimed is:

1. A variant yeast comprising a strain of *Saccharomyces cerevisiae* that is capable of growth utilizing at least one pentose sugar as a sole carbon source in the presence of at least 0.03% wt. 2-deoxy-glucose, wherein the variant yeast is deficient in a gene product of at least one gene selected from the group consisting of GRR1, REG1, and HXK2, and wherein the strain of *Saccharomyces cerevisiae* is Fermentis Ethanol Red.

2. The variant yeast according to claim 1, wherein the strain of *S. cerevisiae* is haploid or diploid.

3. A method for isolating a yeast that will grow on at least one pentose sugar as a sole carbon source, the method comprising the steps of:
   providing a growth medium, wherein the medium includes 2-deoxy-glucose, D-xylose and glutamine, wherein D-xylose is the sole carbon source;
   inoculating the medium with at least one strain of yeast, wherein yeast of the at least one strain are deficient in a gene product of at least one gene selected from the group consisting of GRR1, REG1, and HXK2, and wherein the strain of *Saccharomyces cerevisiae* is Fermentis Ethanol Red; and
   isolating at least one yeast cell from the medium, wherein the yeast cell grows on D-xylose as a sole carbon source in the presence of at least about 0.03 wt. % 2-deoxy-glucose.

4. The method according to claim 3, wherein the strain exhibits detectable growth on the medium after about 14 days.

5. The method according to claim 3, wherein the medium includes about 2.0 wt. % xylose, and about 0.5 wt. % glutamine.

6. The method according to claim 3, where the *S. cerevisiae* is haploid or diploid.

7. A method of fermenting a sugar source, comprising the steps of: providing at least one strain of *Saccharomyces cerevisiae*, wherein yeast of the at least one strain of *Saccharomyces cerevisiae* are deficient in a gene product of at least one gene selected from the group consisting of GRR1, REG1, and HXK2, and wherein the at least one strain of *Saccharomyces cerevisiae* is Fermentis Ethanol Red, and will grow on at least one pentose sugar in the presence of at least 0.03 wt. % 2-deoxy-glucose; and supplying a feed stock that includes at least one sugar; and growing said yeast strain the feed stock.

8. The method according to claim 7, wherein the feed stock includes an amount of D-glucose sufficient to support the growth of the yeast strain in the absence of any additional sugar source.

9. The method according to claim 7, wherein the feed stock includes a pentose sugar that can be fermented by said yeast strain.

10. The method according to claim 7, wherein the feed stock includes a pentose sugar that can be fermented by said yeast strain and at least 0.1% 2-deoxy-glucose.

11. The method according to claim 7, wherein the feed stock includes a fermentable hexose sugar other than D-glucose.

12. The method according to claim 11, wherein the feed stock further includes D-glucose.

* * * * *